(12) United States Patent
Sakaguchi

(10) Patent No.: US 7,083,604 B2
(45) Date of Patent: Aug. 1, 2006

(54) BRIEF-TYPE DIAPER HAVING A SEAMLESS CONFIGURATION

(75) Inventor: Satoru Sakaguchi, Kagawa (JP)

(73) Assignee: Uni-Charm Corporation, Ehime-ken (JP)

( * ) Notice: Subject to any disclaimer, the term of this patent is extended or adjusted under 35 U.S.C. 154(b) by 0 days.

(21) Appl. No.: 10/993,152

(22) Filed: Nov. 22, 2004

(65) Prior Publication Data

US 2005/0131365 A1    Jun. 16, 2005

Related U.S. Application Data

(63) Continuation of application No. PCT/JP03/06292, filed on May 20, 2003.

(30) Foreign Application Priority Data

May 22, 2002   (JP)   ............................. 2002-147757

(51) Int. Cl.
*A61F 13/15*   (2006.01)
*A61F 13/20*   (2006.01)

(52) U.S. Cl. ................................. 604/396; 604/385.24

(58) Field of Classification Search ........... 604/385.01, 604/385.24, 385.29, 393, 394, 396, 385.19, 604/385.3, 395; D24/126

See application file for complete search history.

(56) References Cited

U.S. PATENT DOCUMENTS

| | | | |
|---|---|---|---|
| 2,748,772 A * | 6/1956 | Titone et al. | 604/396 |
| 3,599,638 A * | 8/1971 | Rickard | 604/396 |
| 3,608,551 A * | 9/1971 | Seijo | 604/396 |
| 3,852,827 A * | 12/1974 | Colbert, Jr. | 2/409 |
| 4,771,483 A * | 9/1988 | Hooreman et al. | 2/237 |
| 4,846,822 A * | 7/1989 | Foxman | 604/370 |
| 5,416,929 A * | 5/1995 | Braunstein | 2/406 |
| 6,041,446 A * | 3/2000 | Braunstein et al. | 2/400 |
| 2004/0092904 A1* | 5/2004 | Macedo et al. | 604/396 |

FOREIGN PATENT DOCUMENTS

| | | | |
|---|---|---|---|
| FR | 2 412 275 | * | 7/1979 |
| GB | 2 268 389 A | * | 12/1994 |
| JP | 57-48205 | | 3/1982 |
| JP | 61-207605 | | 9/1986 |
| JP | 61-502264 | | 10/1986 |
| JP | 7-501246 | | 2/1995 |
| JP | 10-168729 | | 6/1998 |
| WO | WO 02/32363 A2 * | | 4/2002 |

* cited by examiner

*Primary Examiner*—Tatyana Zalukaeva
*Assistant Examiner*—Michael G. Bogart
(74) *Attorney, Agent, or Firm*—Lowe Hauptman Berner LLP

(57) ABSTRACT

A brief-type diaper includes an outer layer sheet, an inner layer sheet, an absorber, an elastic member, and a pair of leg openings. The outer layer sheet has a substantially cirqular external shape, the elastic member is stretched on the upper surface of the outer layer sheet along the outer circumferential fringe thereof. When the elastic member contracts, the brief-type diaper is formed with a waist opening free of joints.

7 Claims, 10 Drawing Sheets

BRIEF-TYPE DIAPER HAVING A SEAMLESS CONFIGURATION

CROSS-REFERENCE TO RELATED APPLICATIONS

This application is a Continuation of International Application No. PCT/JP2003/06292 filed May 20, 2003, which application published in Japanese on Nov. 27, 2003 as WO 2003/096949 A1 under PCT Article 21 (2). The International Application PCT/JP2003/06292 is based upon and claims the benefit of priority from Japanese Patent application No.2002-147757 filed on May 22, 2002, the entire contents of which is incorporated herein by reference.

FIELD OF THE INVENTION

The present invention relates to a brief-type diaper to be used as a diaper for an infant, an adult, or a person suffering incontinence. More specifically, the invention relates to a disposable diaper which has a waist opening section and leg opening sections but does not have any cemented sections.

RELATED ART

As shown in FIGS. 9 and 10, a conventional brief-type diaper 1' comprises an abdominal section 50', a back section 52', and leg opening sections 51'. The brief-type diaper 1' is formed by stacking and sealing an absorbent 3' wrapped with a top sheet member web 8' onto an outer layer section web 2' on which elastic members 4' are provided in a stretched manner. The abdominal section 50' and the back section 52' are fixedly cemented together, thereby forming one waist opening section 6' and a pair of leg opening sections 7'. In the brief-type diaper 1', the waist opening section 6' and the leg opening sections 7' are formed elastically, thereby conforming to the shape of a wearer's body. The wearer can usually wear such a brief-type diaper 1' while standing up. The brief-type diaper 1' is used as a brief-type diaper for an infant or for training purpose and also as a diaper for a person suffering incontinence or an adult.

As shown in FIGS. 9 and 10, the conventional brief-type diaper has cemented sections 5' which extend from the leg opening sections 7' provided on both sides of a girth to the waist opening section 6'. Presence of the cemented sections 5' is inevitable, because the abdominal section 50' and the back section 52' of the outer layer section web 2' are fixedly cemented together, thereby forming a brief-type diaper. At the respective cemented sections 5', a portion of outer layer section web 2' and another portion of the same overlap each other. Further, the cemented sections 5' are formed by means of heat fusing or ultrasonic fusing. For these reasons, the cemented sections 5' possess unwieldy rigidity.

Therefore, when the wearer actually wears the diaper, the fixedly-cemented sections come to areas extending from a waist opening section located on both sides of the wearer's body to the neighborhood of the legs, the wearer sometimes receives an unusual feeling. When the wearer moves, the waist opening section and the neighborhoods of the legs come into contact with the cemented sections 5', thereby greatly enhancing the unusual feeling. On rare occasion, an arm or hand touches the diaper from the outside, which also causes an unusual feeling. Further, presence of the cemented sections 5' renders the appearance of a commodity product poor, which in turn yields an inconvenience of inferior marketability.

Therefore, as can be seen from JP07-501246, a flangeless seam having a length of about one-sixteenth of an inch or less is adopted as a cemented section, wherein a sheet material constituting an outer layer sheet is sealed by means of mechanical energy such as ultrasonic sealing, whereby the diaper assumes the appearance of a garment and unusual feeling is reduced. Although the seam has a small length of about one-sixteenth inches or less, the cemented sections still exist. Further, the seam is formed by means of "mechanical energy" such as ultrasonic sealing, and hence the seam assumes a state achieved when resin fused by an ultrasonic wave has hardened. For this reason, rigidity still remains in the seam. Accordingly, the inconvenience still remains unsolved. As can be seen from JP-A-61-207605, a seam involves an overlap having a comparatively small width, such as third-sixteenths of an inch or one eights of an inch. The overlap is sealed by adoption of a sealing method such as sonic sealing, heat sealing, or an adhesive. As a result, the cemented section resembles a line when viewed from the outside. Therefore, the cemented section does not impair the appearance much. However, the cemented section is formed by sealing a plane overlap, and hence the cemented section still remains. For this reason, the inconvenience still remains unsolved.

SUMMARY OF THE INVENTION

The invention has been conceived to solve the above-described problem, and the object of the invention is to provide a brief-type diaper not having a cemented section in the direction of a girth.

To solve the problem, the invention is characterized in that an outer layer sheet constituting a brief-type diaper has an elastic member which has been extended beforehand is continuously bonded to a traveling sheet and that the thus-extended elastic member undergoes contraction, thereby constituting a ring-shaped waist opening section.

More specifically, the elastic member is arranged continuously while drawing a curve such as a waveform pattern or a straight line. The elastic member is provided continuously in a stretched manner along a substantially outer peripheral edge of the outer layer sheet. In contrast with a conventional brief-type diaper in which an abdominal section of the outer layer sheet and a rear section of the same are fixedly cemented together, a continuous ring-shaped waist opening section can be formed. On the basis of this finding, the present inventors have come to complete the present invention.

Moreover, the brief-type diaper of the invention is provided on the basis of the novel idea that previously-extended elastic members are provided on a traveling sheet in a stretched manner so as to draw two curves or two straight lines such that the two curves, such as waveforms, or straight lines cross each other or come in close proximity to each other, thereby forming an outer layer sheet.

More specifically, the invention provides the following features:

(1) A brief-type diaper having an outer layer sheet constituting an exterior, an inner layer sheet which comes into contact with a wearer, an absorbent for absorbing body fluids, an elastic member for causing portions of the outer and inner sheets to contract and extend, and a pair of leg openings through which the wear's legs penetrate, wherein the absorbent is arranged such that at least a portion of the absorbent is located between the pair of leg openings; and either the outer layer sheet or the inner layer sheet or both outer and inner layer sheets are formed from members which are seamless in the direction of a girth when the diaper is worn.

According to the brief-type diaper of the invention (1), the absorbent is arranged such that at least a portion of the absorbent is located between the pair of leg openings; and either the outer layer sheet constituting an outer layer or the inner layer sheet which is brought into contact with the wearer's skin or both outer and inner layer sheets are formed from members which are seamless in the direction of a girth when the diaper is worn. Therefore, the necessity for fixedly cementing together an abdominal section and a rear section of a diaper, which has hitherto been required by a conventional brief-type diaper, is eliminated. Therefore, no cemented section is present in the direction of a girth or other directions. Further, a portion of the absorbent is present at least between the pair of leg opening sections. Hence, the absorbent is suitable for absorbing excretions such as urine.

(2) The brief-type diaper according to (1), wherein the diaper is formed from the outer layer sheet, the elastic member which is provided beforehand along a substantially outer peripheral edge of the outer layer sheet in an elongated state and on a surface facing a wearer when the wearer has worn the diaper, the inner layer sheet provided integrally with the outer layer sheet and the surface of the elastic member facing the wearer, and the absorbent provided at substantially the center of the surface of the inner layer sheet facing the wearer; wherein the elastic member is subjected to shrinkage, thereby constituting a waist opening section.

According to the brief-type diaper of the invention (2), the diaper is formed from the outer layer sheet constituting an outer layer, the elastic member which is provided beforehand along a substantially outer peripheral edge of the outer layer sheet in an elongated state and on a surface facing a wearer when the wearer has worn the diaper, the inner layer sheet provided integrally with the outer layer sheet and the surface of the elastic member facing the wearer, and the absorbent provided at substantially the center of the surface of the inner layer sheet facing the wearer.

Therefore, the elastic member that has been provided beforehand along an outer peripheral edge of the outer layer sheet in an extended state between the outer layer sheet and the inner layer sheet undergoes contraction, thereby forming a waist opening section. Thus, a brief-type diaper is formed. Since the outer layer sheet and the inner layer sheet have no seam, the brief-type diaper has no cemented section in the direction of a girth or other directions. As a result of the elastic member being sandwiched between the outer layer sheet and the inner layer sheet, the elastic member is fixed without fail. Moreover, the elastic member is provided in a stretched manner along the outer peripheral edge of the sheet, thereby rendering the waist opening section large.

(3) The brief-type diaper according to (2), further comprising a liquid-impervious sheet provided between the outer layer sheet and the inner layer sheet and at substantially the center of the these sheets.

According to the brief-type diaper of the invention (3), a liquid-impervious sheet is provided between outer layer sheet and inner layer sheet and at substantially the center of these sheets.

As a result, even if body fluids, such as urine, absorbed by the absorbent core may have leaked, a liquid-impervious sheet provided between the outer layer sheet and the inner sheet prevents seepage of the body fluids. Further, provision of the liquid-impervious sheet between the outer layer sheet and the inner layer sheet facilitates a change in the size of the liquid-impervious sheet. It is also possible to make the sheet large, to thereby provide resistance against seepage of body fluids such as urine, as required. Further, it is possible to make the sheet small, to thereby reduce material to be used, as required. When the liquid-impervious sheet having a pattern like design printed thereon is used, the number of sheets covering a designed surface is small, and hence a printed design becomes easy to see.

(4) The brief-type diaper according to (1), wherein the diaper is formed from the outer layer sheet, the elastic member which is provided beforehand along a substantially outer peripheral edge of the outer layer sheet in an elongated state and on a surface facing a wearer when the wearer has worn the diaper, the absorbent provided at substantially the center of the surface of the inner layer sheet facing the wearer, and the inner sheet which is substantially identical in shape and size with the outer layer sheet, and has an opening section located at substantially the center thereof, is provided integrally with the outer layer sheet and the surface of the elastic member facing the wearer such that an opening section covers an outer peripheral edge of the outer layer sheet; wherein the elastic member is subjected to shrinkage, thereby constituting a waist opening section.

According to the brief-type diaper of the invention (4), the diaper is formed from the outer layer sheet constituting an outer layer, the elastic member which is provided beforehand along a substantially outer peripheral edge of the outer layer sheet in an elongated state and on a surface facing a wearer when the wearer has worn the diaper, the absorbent provided at substantially the center of the surface of the inner layer sheet facing the wearer, and the inner sheet which is provided integrally with the outer layer sheet and the surface of the elastic member facing the wearer such that an opening section covers an outer peripheral edge of the outer layer sheet, is substantially identical in shape and size with the outer layer sheet, and has an opening section located at substantially the center thereof.

Therefore, the elastic member that has been provided beforehand in a stretched manner along the outer peripheral edge of the outer and inner layer sheets undergoes contraction, thereby forming a waist opening section. In this way, a brief-type diaper is formed. However, the outer layer sheet and the inner layer sheet have no seam. Hence, the brief-type diaper has no cemented section in the direction of a girth or other directions. Further, the periphery of the absorbent can be covered with a hydrophobic inner layer sheet, thereby further preventing leakage from an end of the absorbent.

(5) The brief-type diaper according to (4), wherein a back sheet of the absorbent is made substantially identical in size and shape with the outer layer sheet and is placed between the elastic member and the inner layer sheet.

According to the brief-type diaper of the invention (5), an absorbent, comprised of liquid-impervious back sheet, is made substantially identical in size and shape with the outer layer sheet and is placed between the elastic member and the inner layer sheet. Therefore, even if body fluids, such as urine, have leaked, seepage of the fluids can be prevented to a greater extent, because the entire outer layer sheet is covered with the liquid-impervious back sheet.

(6) The brief-type diaper according to (1), wherein the diaper is formed from the donut-shaped outer layer sheet having an opening section formed at substantially the center thereof, the elastic member which is provided beforehand along a substantially outer peripheral edge of the outer layer sheet in an elongated state and on a surface facing a wearer, the inner layer sheet which is provided integrally with the outer layer sheet and the surface of the elastic member facing the wearer, is substantially identical in shape and size with the outer layer sheet, and has an opening section at substantially a center thereof, and the absorbent provided on a surface of the outer layer sheet, the surface facing the wearer, so as to straddle an opening in the opening section and opening portions left on both sides of the opening section; the elastic member is subjected to contraction, thereby forming a waist opening; and the opening portions which are left on both sides of the opening section constitute the leg opening sections.

According to the brief-type diaper of the invention (6), the diaper is formed from the donut-shaped outer layer sheet having an opening section formed at substantially the center thereof, the elastic member which is provided beforehand along a substantially outer peripheral edge of the outer layer sheet in an elongated state and on a surface facing a wearer, the inner layer sheet which is provided integrally with the outer layer sheet and the surface of the elastic member facing the wearer, is substantially identical in shape and size with the outer layer sheet, and has an opening section at substantially a center thereof, and the absorbent provided on a surface of the outer layer sheet, the surface facing the wearer, so as to straddle an opening in the opening section and opening portions left on both sides of the opening section.

Therefore, the elastic member that has been provided beforehand in a stretched manner along the outer peripheral edge of the outer and inner layer sheets undergoes contraction, thereby forming a waist opening section. In this way, a brief-type diaper is formed. However, the outer layer sheet and the inner layer sheet have no seam. Hence, the brief-type diaper has no cemented section in the direction of a girth or other directions. Further, the leg opening sections are formed by opening sections left on both sides of the absorbent when the absorbent is placed on the sheet. Hence, the leg openings can be made large, thereby facilitating passage of the wearer's legs and allowing the wearer to move easily. Since the number of generating openings can be reduced, and the size of the openings is large, the openings can be readily opened.

(7) The brief-type diaper according to any one of (1) through (6), the elastic member provided at the waist opening section has a front abdominal region and a rear abdominal region along the waist, or at a right abdominal region and a left abdominal region crossed to each other along the waist opening section.

According to the brief-type diaper of the invention (7), the elastic member provided on the waist opening section has a cross at a front abdominal region and a rear abdominal region along the waist, or at a right abdominal region and a left abdominal region along the waist. The elastic member becomes continuous at the position of intersection. Therefore, as a result of the continuous elastic member undergoing contraction, a ring-shaped waist opening section is formed, whereby a brief-type diaper is formed. However, the elastic member is provided along the outer peripheral edge of the outer layer sheet in a stretched manner regardless of whether the intersection of the elastic member is located in the front and rear abdominal regions or in the right and left abdominal regions. Similarly, the ring-shaped waist opening section is formed, whereby a seamless brief-type diaper can be obtained.

Here, the term "waist opening section" means a part of the diaper which conforms to a position on the body above the hip bone upon wearing them. Further, the term "girth" means a part of the diaper which conforms to the area of the body ranging from the hip bone to the crotch. Further, the term "front abdominal region" means a surface of a brief-type diaper facing an abdomen of the body (In other words, abdominal region is brought into contact upon wearing them), and the term "rear abdominal region" means a surface of the brief-type diaper facing the back of the body (In other words, back of the body is brought into contact upon wearing them). Further, "right abdominal region" means a surface of the brief-type diaper facing the right side of body (In other words, right side of the body is brought into contact upon wearing them), and the term "left abdominal region" means a surface of the brief-type diaper facing the left side of body (In other words, left side of the body is brought into contact upon wearing them) In addition, "cross" means a straight lines crossing each other including the two or more straight line crossing at a point, each individual straight line crossing with each other, and straight line brought into contact with each other.

(8) The brief-type diaper according to any one of (1) through (6), the elastic member provided along the waist opening section has a cross or an overlap at a front abdominal region and a rear abdominal region along the waist, or at a right abdominal region and a left abdominal region along the waist.

According to the brief-type diaper of the invention (8), the elastic member provided along the waist opening section has a cross or overlap at a front abdominal region and a rear abdominal region along the waist, or at a right abdominal region and a left abdominal region along the waist. The elastic member becomes continuous at the position of intersection. Therefore, as a result of the continuous elastic member undergoing contraction, a ring-shaped waist opening section is formed, whereby a brief-type diaper is formed. However, the elastic member is provided along the outer peripheral edge of the outer layer sheet in a stretched manner regardless of whether the intersection of the elastic member is located in the front and rear abdominal regions or in the right and left abdominal regions. Similarly, the ring-shaped waist opening section is formed, whereby a seamless brief-type diaper can be obtained.

(9) The brief-type diaper according to any one of (1) through (8), the elastic member is rubber yarn, flat rubber, or a ribbon-shaped elastic body.

According to the brief-type diaper of the invention (9), the elastic member is embodied as a yarn-shaped, flat, or ribbon-shaped elastic substance. The elastic member is extensible. If the elastic member has been provided beforehand in a stretched manner, the elastic member becomes contracted when released. The outer peripheral edge of the outer layer sheet and that of the inner layer sheet are pulled by the elastic member, thereby forming a ring-shaped waist opening section. Thus, a seamless brief-type diaper is produced.

(10) The brief-type diaper according to any one of (1) through (9), the absorbent is laminated and cemented onto a side surface of either the outer layer sheet or the inner layer sheet facing the wearer.

According to the brief-type diaper of the invention (10), the absorbent is laminated and cemented onto a side surface of either the outer layer sheet or the inner layer sheet facing the wearer. Therefore, when a brief-type diaper is formed, the absorbent is located so as to extend from the crotch section to the front and rear abdominal regions. Therefore, the absorbent is present at the crotch section and becomes suitable for absorbing excretions such as body fluids.

(11) The brief-type diaper according to any one of (1) through (10), the absorbent comprises a liquid-pervious top sheet, and an absorbent core which is placed adjacent to the top sheet and absorbs liquid having passed through the top sheet, wherein a three-dimensional leakage prevention wall is provided at longitudinal side edges of the top sheet.

According to the brief-type diaper of the invention (11), the absorbent, comprises at least a liquid-pervious top sheet, an absorbent core which is placed adjacent to the top sheet and absorbs liquid having passed through the top sheet; and a three-dimensional leakage prevention wall is provided at longitudinal side edges of the top sheet. Therefore, body fluids, such as urine, are absorbed by an absorbent core. Further, the three-dimensional leakage prevention wall provided at the longitudinal edges of the absorbent core prevents leakage of the body fluids from both sides of the absorbent core.

DESCRIPTION OF THE PREFERRED EMBODIMENT

Embodiments of the invention will now be described by reference to the drawings.

First Embodiment

Figure 1:
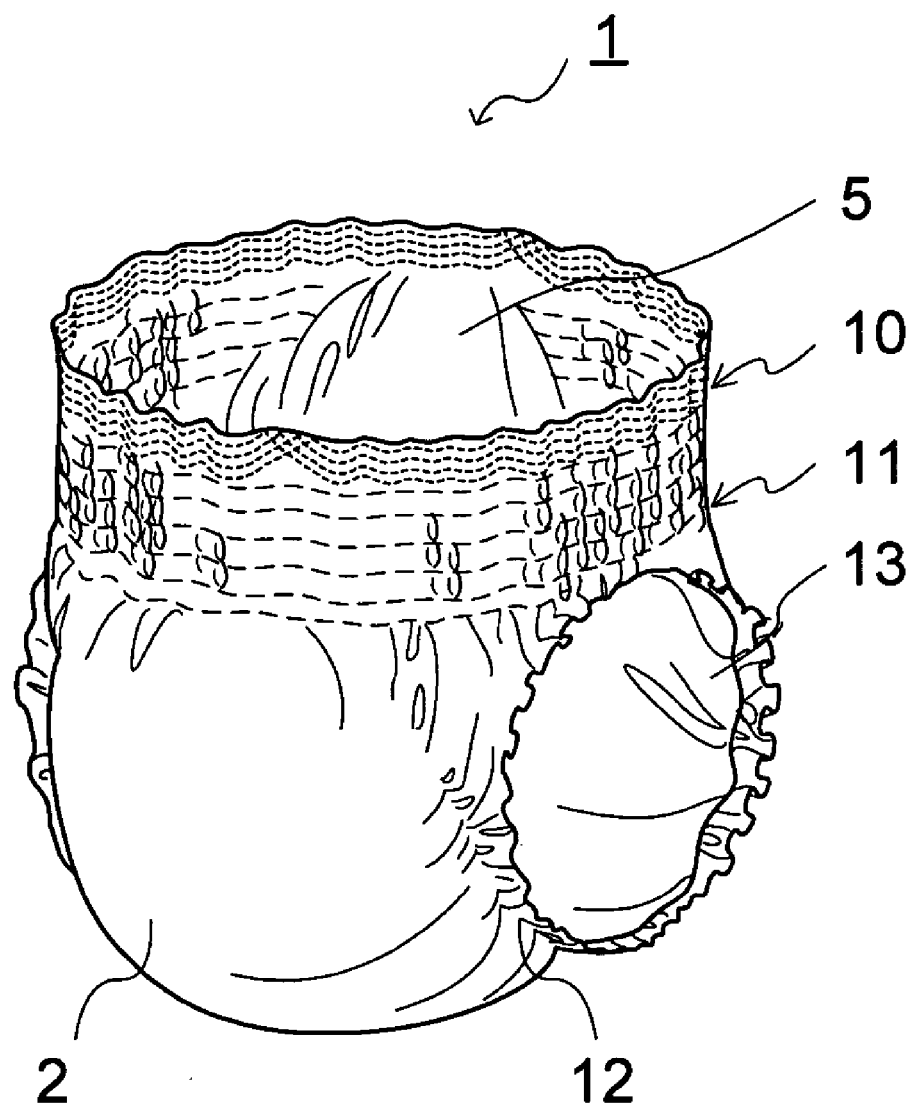
FIG. 1 is a perspective view showing a first embodiment of a brief-type diaper according to the invention.
Figure 2A:
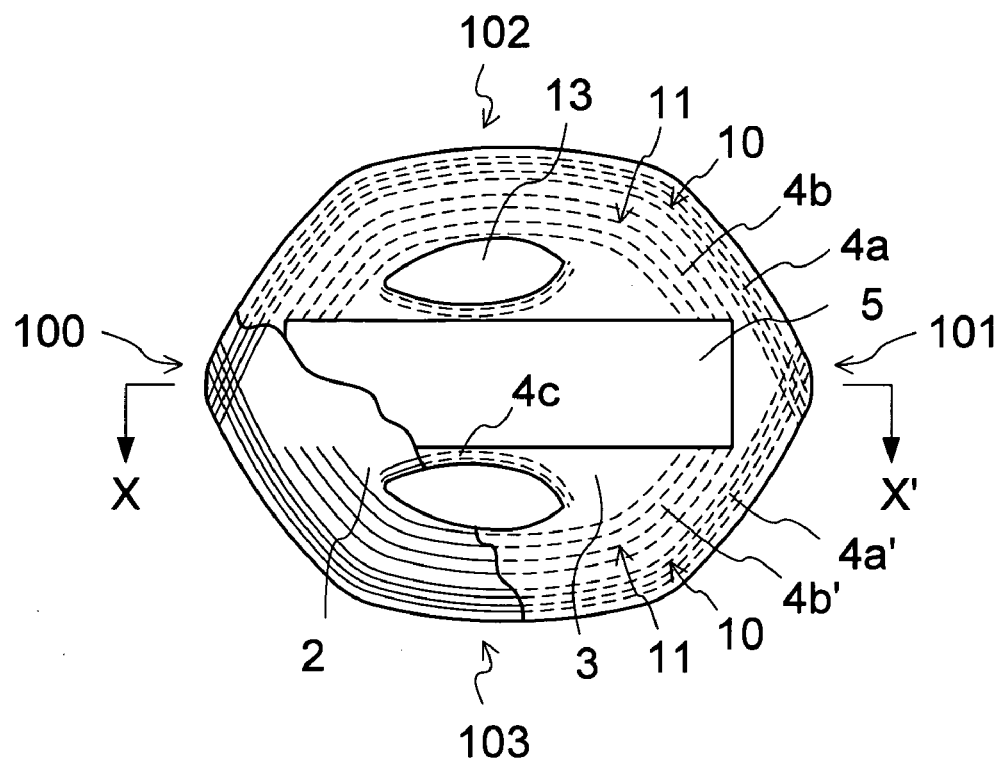
FIG. 2A is a partial fragmentary developed plan view of first embodiment of the brief-type diaper of the present invention.
Figure 2B:
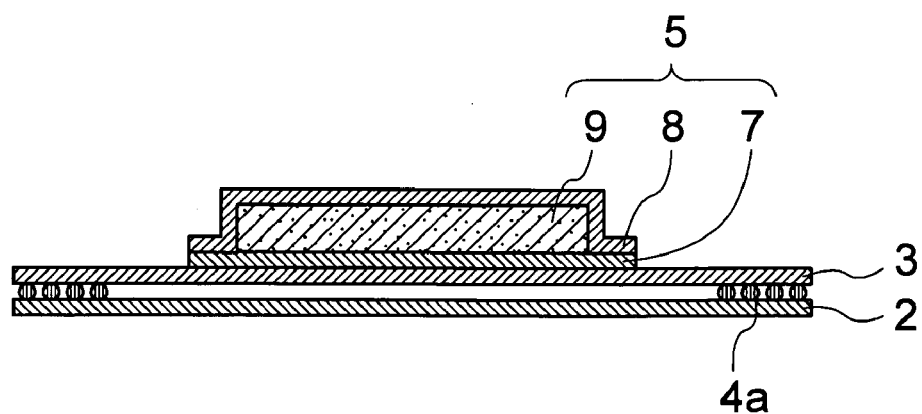
FIG. 2B is a cross-sectional view of the diaper taken along line X–X' shown in FIG. 2A.
Figure 3:
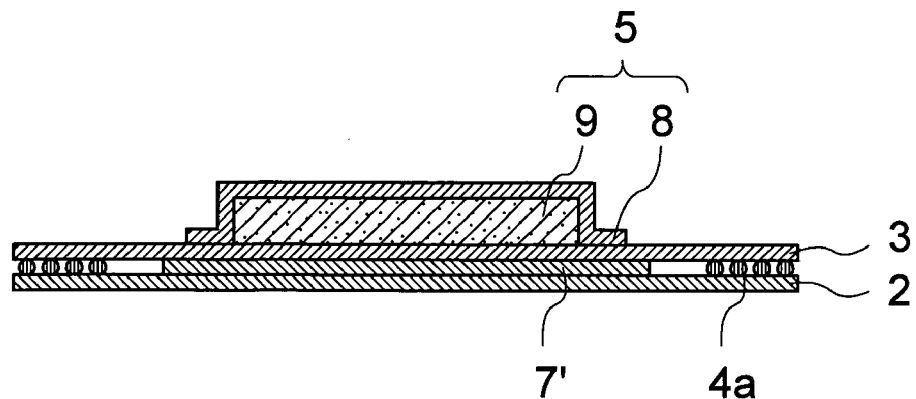
FIG. 3 is a cross-sectional view of a modification of the embodiment shown in FIG. 2 taken along line X–X'.
Figure 4A:
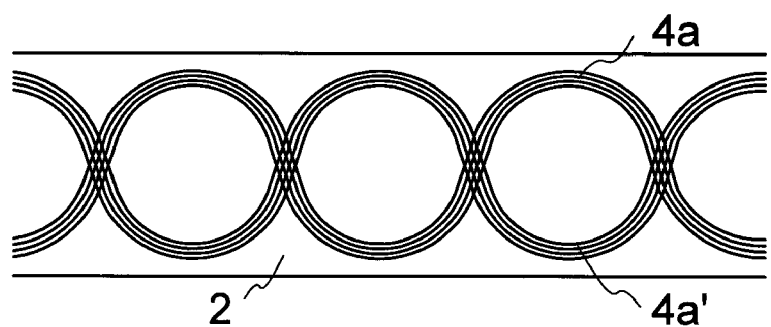
FIG. 4A is a fragmentary plan view of first carried out example showing flow of an elastic member provided on an outer layer sheet in a stretched manner.
Figure 4B:
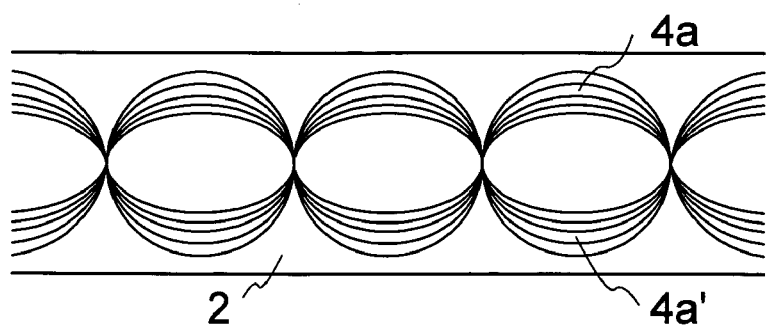
FIG. 4B is a fragmentary plan view of second carried out example showing flow of an elastic member provided on an outer layer sheet in a stretched manner.
Figure 4C:
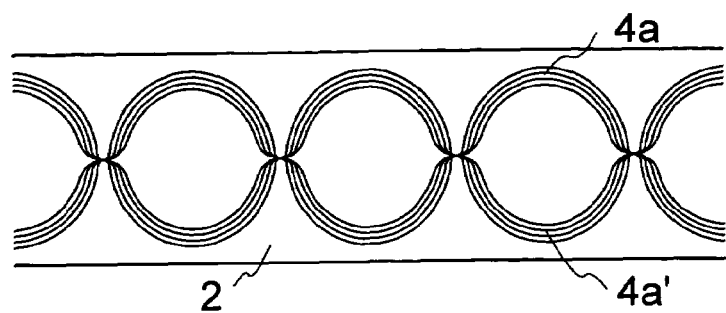
FIG. 4C is a fragmentary plan view of third carried out example showing flow of an elastic member provided on an outer layer sheet in a stretched manner.
Figure 4D:
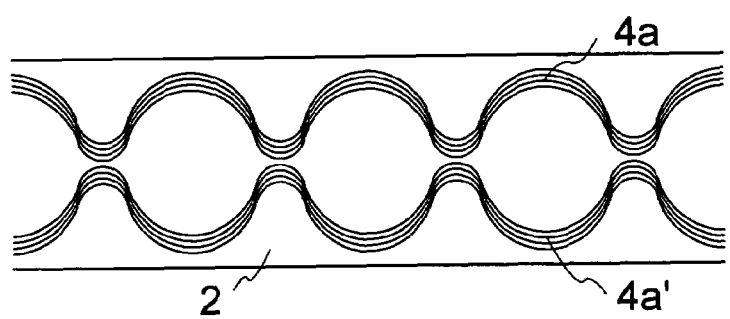
FIG. 4D is a fragmentary plan view of fourth carried out example showing flow of an elastic member provided on an outer layer sheet in a stretched manner.
Figure 4E:
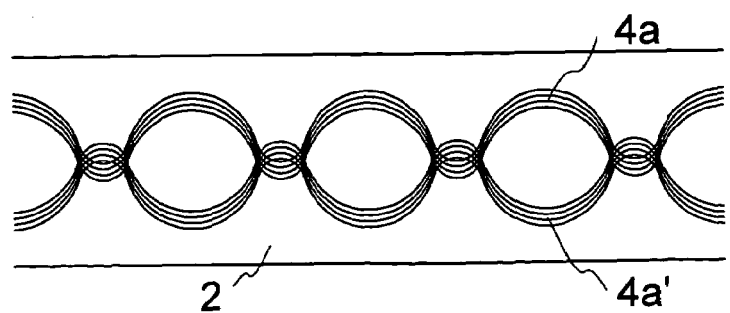
FIG. 4E is a fragmentary plan view of fifth carried out example showing flow of an elastic member provided on an outer layer sheet in a stretched manner.
Figure 5A:
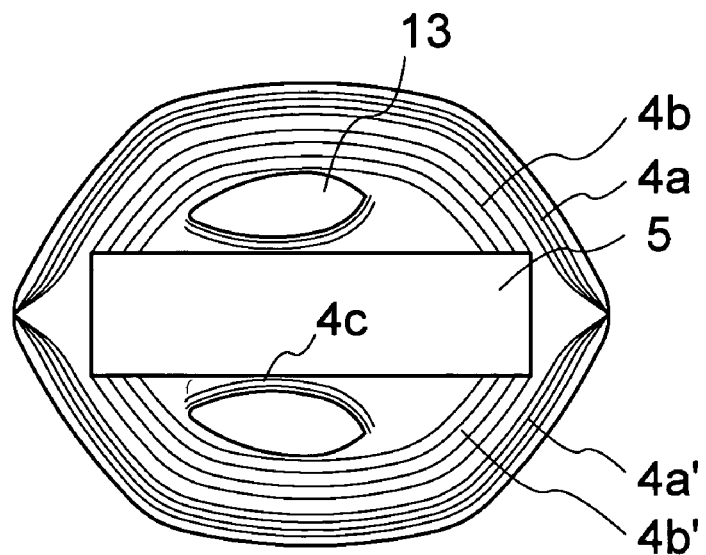
FIG. 5A is a developed plan view showing first modified example of first embodiment as shown in FIG. 2A.
Figure 5B:
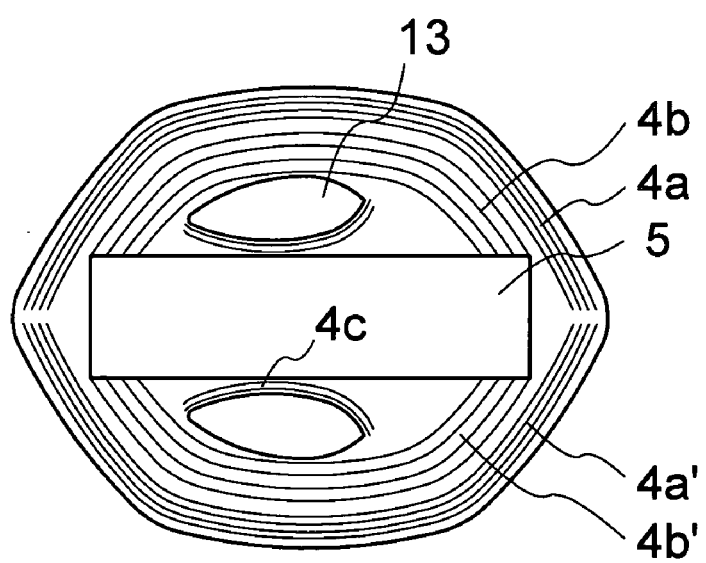
FIG. 5B is a developed plan view showing second modified example of first embodiment as shown in FIG. 2A.
Figure 5C:
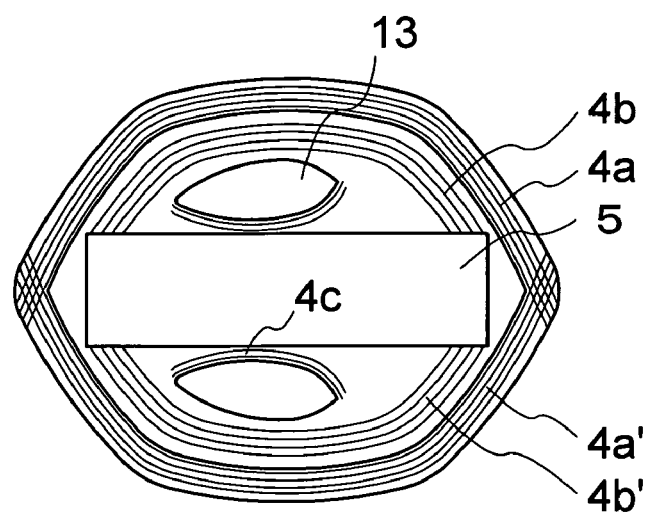
FIG. 5C is a developed plan view showing third modified example of first embodiment as shown in FIG. 2A.
Figure 5D:
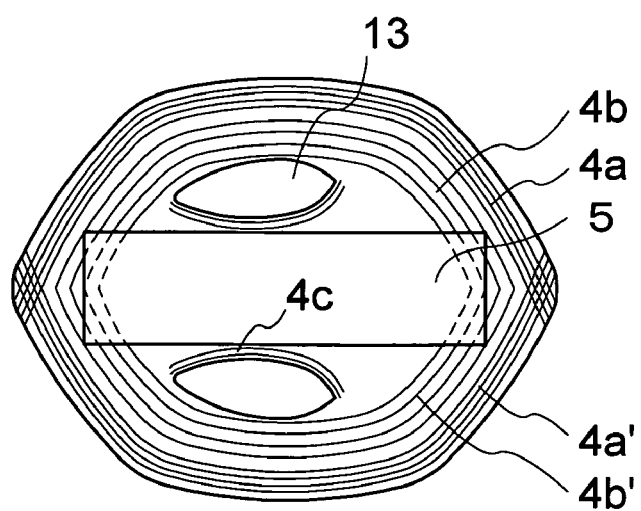
FIG. 5D is a developed plan view showing fourth modified example of first embodiment as shown in FIG. 2A.

FIG. 1 is a perspective view showing an first embodiment of a brief-type diaper according to the invention; FIG. 2A is a partial fragmentary developed plan view of first embodiment of the brief-type diaper of the present invention, and FIG. 2B is a cross-sectional view of the diaper taken along line X–X' shown in FIG. 2A; FIG. 3 is a cross-sectional view of a modification of the embodiment shown in FIG. 2 taken along line X–X'; and FIG. 4A is a fragmentary plan view of first carried out example showing flow of an elastic member provided on an outer layer sheet in a stretched manner. FIG. 4B is a fragmentary plan view of second carried out example showing flow of an elastic member provided on an outer layer sheet in a stretched manner. FIG. 4C is a fragmentary plan view of third carried out example showing flow of an elastic member provided on an outer layer sheet in a stretched manner. FIG. 4D is a fragmentary plan view of fourth carried out example showing flow of an elastic member provided on an outer layer sheet in a stretched manner. FIG. 4E is a fragmentary plan view of fifth carried out example showing flow of an elastic member provided on an outer layer sheet in a stretched manner. FIG. 5A is a developed plan view showing first modified example of first embodiment as shown in FIG. 2A; FIG. 5B is a developed plan view showing second modified example of first embodiment as shown in FIG. 2A; FIG. 5C is a developed plan view showing third modified example of first embodiment as shown in FIG. 2A; and FIG. 5D is a developed plan view showing fourth modified example of first embodiment as shown in FIG. 2A.

As shown in FIG. 1, a brief-type diaper 1 of the embodiment comprises a waist opening section 10 for a wearer, a girth section 11, and leg sections 12. An absorbent 5 for housing and retaining excretions, such as urine, is stacked on and cemented to the elasticized outer layer sheet 2. FIG. 2A shows a developed state of the brief-type diaper 1 when a waist opening section 10 is broadened. As shown in FIGS. 2A and 2B, the brief-type diaper 1 of the embodiment comprises an outer layer sheet 2 assuming a substantially-circular outer shape constituting outer layer; an inner layer sheet 3 which is substantially identical in size and shape with the outer layer sheet 2 which is brought into contact with wearer's skin; elastic members 4a, 4a'4b, 4b', stretched between the sheets 2 and 3; and an absorbent 5 provided substantially at the center of the inner layer sheet 3. More specifically, in order to make the waist opening section 10 and girth sections 11 of the diaper elastic, a plurality of elastic members 4a are provided in a stretched manner between the outer layer sheet 2 and the inner layer sheet 3 and across the entire right abdominal region 102 along the waist opening section 10 so as to follow an outer peripheral edge of the outer layer sheet 2. Further, a plurality of elastic members 4a' are provided in the same manner across the entire left abdominal region 103. Thus, the elastic members 4a, 4a' constitute a waist gather. Moreover, a plurality of elastic members 4b are provided in a stretched manner across the entire right abdominal region 102 along the girth, and a plurality of elastic members 4b' are provided in a stretched manner across the entire left abdominal region 103. Thus, the elastic members 4b, 4b' constitute a girth gather. The size of the inner layer sheet 3 is not limited to a substantially-identical size as outer layer sheet 2, described in connection with this embodiment; the inner layer sheet 3 may assume any size, so long as the sheet can cover the elastic members 4a, 4a'.

As shown in FIG. 4A, the plurality of elastic members 4a provided along the waist opening section 10 across the entire right abdominal region 102 and the plurality of elastic members 4a' provided along the waist across the entire left abdominal region 103 are laid in a stretched manner on the continuously-supplied outer layer sheet 2 so as to assume substantial sinusoidal waveforms and such that the elastic members 4a, 4a'cross each other one by one and the waveforms become tied together. The continuously-supplied inner layer sheet 3 is laid integrally on the surface of the outer layer sheet 2 having the elastic members 4a, 4a' provided in a stretched manner, the surface facing the wearer. The thus-continuously-formed sheet member is finally separated into pieces along areas where the elastic members 4a, 4a' cross each other, thereby forming brief-type diapers. As a result, the elastic members 4a, 4a' cross each other and are connected together at a front abdominal region 100 (i.e., an abdominal section) and a rear abdominal region 101 (i.e., a back section), and thus continue along the outer peripheral edges of the outer and inner layer sheets. Further, the elastic members 4a, 4a' are provided beforehand in a stretched manner. Hence, when the elastic members 4a, 4a' provided along the waist opening section 10 in a stretched manner are subjected to contraction, the outer peripheral edges of the outer and inner layer sheets 2, 3 are pulled, thereby constituting a continuous ring-shaped waist opening section 10.

In the embodiment, the elastic members 4a, 4a' provided along the waist opening section 10 crossing each other and become tied together. However, the invention is not limited to the embodiment. As shown in FIG. 5A, the elastic members 4a, 4a' may be laid in a stretched manner so as to be tied together while crossing or overlapping each other at a point. As shown in FIG. 4B, this may also be achieved by laying the elastic members 4a, 4a' on the continuously-supplied outer layer sheet 2 such that two curves cross each other at a point, or as shown in FIG. 4C by laying the elastic members 4a, 4a' in a stretched manner on the continuously-supplied outer layer sheet 2 such that two curves come into contact with each other at valleys and peaks.

The shapes of the two curves are not limited to those shown in FIGS. 4A through 4E. The two curves shown may assume any shape, so long as the curves follow the outer shape of the outer layer sheet 2. For instance, if the outer layer sheet 2 assumes a polygonal shape, the curves may assume a kinked line matching the polygonal shape. In the embodiment, the outer layer sheet 2 assumes a substantially-circular outer shape, and hence the two curves are made so as to assume a substantial sinusoidal waveform pattern matching the circular shape. However, the curves are not limited to such a waveform pattern. The curves may assume any shape, so long as the curves follow the outer shape of the outer layer sheet 2.

Elastic member 4a, 4a' provided at the waist opening section 10 laid in stretched manner as shown in FIG. 5B, the curves may be discontinuous such that separated in portion. More specifically, when the elastic members 4a, 4a' are continuously arranged in a stretched manner along the waist opening section 10 and fixedly bonded to the outer layer sheet 2, intersecting portions of the elastic members 4a, 4a' remain non-bonded. When the continuous sheet member is cut along the intersecting portions into brief-type diapers, non-bonded section of the elastic members 4a, 4a' may be subjected to contraction and be slightly separated from each other. In this case, the elastic members 4a, 4a' are partially discontinuous. However, the elastic members 4a, 4a' are laid along the outer peripheral edge of the outer layer sheet 2 in a stretched and substantially continuous fashion. Hence, when the elastic members 4a, 4a' provided along the waist opening section 10 undergo contraction, they constitute a ring-shaped waist opening section 10 to develop brief-type diaper. In this case, cross formed from elastic member 4a, 4a' disappear, and hence, the thickness of the elastic members can be reduced when compared with the thickness of the elastic members achieved when intersections are present. Thus, the wearer does not have unusual feeling. As shown in FIG. 4D, this can also be achieved when two curves come close to each other at valleys and peaks on the continuously-supplied outer layer sheet 2. The shapes of the two curves are not limited to those shown in FIG. 4D. The curves may assume any shape, so long as the curves follow the outer shape of the outer layer sheet 2. For instance, when the outer layer sheet 2 assumes a polygonal shape, the curves may assume a shape resembling a kinked graph matching the polygonal shape. More specifically, in the embodiment, the outer layer sheet 2 assumes a substantially-circular outer shape, and hence the two curves are made so as to assume a waveform pattern matching the circular shape. However, the curves are not limited to such a waveform pattern. The curves may assume any shape, so long as the curves follow the outer shape of the outer layer sheet. 2.

As shown in FIG. 5C, the elastic members 4a, 4a' to be laid along the waist opening section 10 in a stretched manner may be provided in a double layer. By means of a double layer structure, fastening the diaper to the waist becomes tight, thereby improving fit. Consequently, even when the diaper has been subjected to vigorous workout, the diaper becomes less likely to slip down.

The elastic members 4b, 4b' provided in the girth 11 are provided at locations outside from both side edges of the absorbent 5 in a stretched manner such that elasticity is exhibited. Stretching of the elastic members 4b, 4b' is also achieved by laying and fixedly bonding the elastic members 4b, 4b' in the same manner in which the elastic members 4a, 4a' are provided along the waist opening section 10. The elastic members 4b, 4b' are joined together as being provided above (FIG. 2A or FIG. 5A through 5C) at areas outside from both side edges of the absorbent 5 in a stretched manner. However, the method is not limited to this. As shown in FIG. 5D, the elastic members 4b, 4b' may be joined one by one on the surface of the absorbent 5 facing the wearer. Moreover, the elastic members may be provided in a stretched manner so as to cross or overlap each other at a point (not shown). Like the elastic members 4a, 4a' to be provided along the waist opening section 10, intersecting portions of the elastic members 4b, 4b' are not fixedly bonded, and hence the elastic members 4b, 4b' may be made discontinuous. Thus, as shown in FIG. 5D, if the elastic members 4b, 4b' to be provided along the girth in a stretched manner are also provided in a stretched manner at areas where the absorbent 5 is present, both longitudinal ends of the absorbent 5 are pressed to the body side by the elastic members 4b, 4b'. For this reason, adhesion between the diaper and the body is improved, thereby preventing leakage of body fluids such as urine to a much greater extent. Moreover, excessive protrusion of the absorbent 5 is prevented, thereby imparting neat and good appearance to a brief-type diaper.

Up to this point, a description has been given of a case where the elastic members 4a, 4a', 4b, 4b' crossing each other at the front and rear abdominal regions, 100, 101. The elastic members may cross each other at the right and left abdominal regions, 102, 103. Even in this case, the outer layer sheet 2 and the inner layer sheet 3 assume a substantially-circular outer shape. Hence, a brief-type diaper 1 similar to that achieved in the embodiment is formed.

The elastic members 4a, 4a' to be provided along the waist opening section 10 of the outer layer sheet 2 and the elastic members 4b, 4b' to be provided along the girth 11 the same may preferably be stretched so as to differ from each other in terms of degree of extension and stress. Specifically, the elastic members 4a, 4a' to be provided along the waist opening section 10 stretched at higher degree of extension and increased stress. Further, the elastic members 4b, 4b' to be provided along the girth section 11 of the outer layer sheet 2 may preferably be stretched with a low degree of extension and small stress.

As mentioned above, the elastic members 4a, 4a'4b, 4b' added such that the degree of extension and stress change from the waist opening section 10 and girth 11 thereby enabling the diaper to conform more closely to the shape of the body. Specifically, the waist opening section 10 of the diaper can be fastened to such an extent that a diaper does not slip down when being worn and conforms to the wearer. Since the girth 11 can gently conform to the wearer, the way to stretch the elastic members is preferable. A method for changing the fitness of the waist opening section 10 of the diaper and that of the girth may also be achieved by selecting the number of elastic members, intervals at which the elastic members 4a, 4a', 4b, 4b' are to be stretched, the thickness of the elastic members, and materials of the elastic members, as required rather than changing the degree of extension of the elastic members.

In the embodiment, the elastic members 4a, 4a', 4b, 4b' to be provided along the waist opening section 10 and those to be provided along the girth 10 are set so as to differ from each other in terms of the degree of extension and stress. However, the same degree of extension or the same stress may also be employed.

A pair of leg opening sections 13 are formed at positions on the outer and inner layer sheets 2, 3, wherein the positions are symmetrical about the absorbent 5. A plurality of elastic members 4c to be used for forming a leg gather are provided in a stretched manner along the side edge of each leg opening section 13, the side edge facing a crotch region. Adoption of the construction is effective for enhancing adhesion of the leg gather to the neighborhood of the leg 12 and preventing leakage of urine from the space surrounding the legs 12.

Both longitudinal ends of the liquid permeable top sheet 8 of the absorbent 5 are preferably provided with a leakage prevention wall (not shown), wherein the elastic members are provided in a stretched manner along the respective upper side edges of the leakage prevention walls. The leakage prevention wall is formed from a nonwoven fabric cloth, thereby preventing leakage of body fluids absorbed by an absorbent core from both sides of the absorbent core.

The top sheet 8 may assume a structure shown in FIG. 3, wherein the liquid-impervious sheet 7', for example, liquid-impervious back sheet 7 comprising absorbent 5, is provided at substantially a center position between the outer layer sheet 2 and the inner layer sheet 3. As a result, even if body fluids, such as urine, absorbed by the absorbent core 9 may have leaked, a liquid-impervious sheet 7' provided between the outer sheet 2 and the inner sheet 3 prevents seepage of the body fluids. Further, provision of the liquid-impervious sheet 7' between the outer layer sheet 2 and the inner layer sheet 3 facilitates a change in the size of the liquid-impervious sheet 7'. It is also possible to make the liquid-impervious sheet 7' large, to thereby provide resistance against seepage of body fluids such as urine, and make the sheet small, to thereby reduce material to be used, as required. When the liquid-impervious sheet 7 having a patterned design printed thereon is used, the number of sheets covering a designed surface is small, and hence a printed design becomes easy to see.

The elastic members 4a, 4a', 4b, 4b' are not limited to any particular material but are formed from any material, so long as the material possesses elasticity; for example, rubber yarn made of natural/synthetic rubber or polyurethane, a ribbon-shaped elastic body, heat-shrinkable material, and water-absorptive shrinkable fibers.

The outer layer sheet 2 and the inner layer sheet 3 are preferably made of gas-permeable nonwoven fabric cloth, more preferably of hydrophobic nonwoven fabric cloth. For example, the nonwoven fabric cloth includes spun bond nonwoven fabric cloth made of polypropylene or the like; through-air nonwoven fabric cloth made of fibers, such as polyethylene fibers, polypropylene fibers, polyethylene terephthalate fibers, or the like; and spun lace nonwoven fabric cloth. In addition, there may also be employed a complex sheet formed from nonwoven fabric cloth—which includes elastomer or copolymer and possesses flexibility and an extensible characteristic—and a flexible film. Moreover, a liquid-impervious plastic film may be sandwiched between the outer layer sheet 2 and the inner layer sheet 3.

The absorbent 5 is formed from a rectangular or guitar-shaped absorbent core 9 which is sandwiched between the liquid-impervious back sheet 7 and the liquid-pervious top sheet 8 such that each longitudinal end of the core is split from a longitudinal center in a transverse direction of the core. The liquid-impervious back sheet 7 is nonwoven fabric cloth which has been subjected to water repellent finishing, a moisture-permeable plastic film having minute pores, or a layered product consisting of the fabric cloth and the plastic film. Nonwoven fabric cloth is usually used for the liquid-pervious top sheet 8. The absorbent core 9 is preferably a core made by combined use of defibrated pulp and water-absorptive polymer. In addition, a core—which is formed from a mixture of cellulose fibers, thermoplastic resin, high-molecular water-absorptive polymer, heat-fusible fibers, and the like and which has been subjected to heat treatment—is also preferable. In the case of an absorbent into which several layers are stacked, a polymer may be located in an upper layer, an intermediate layer, or a lower layer. Alternatively, the polymer may be uniformly mixed with pulp. The water-absorptive polymer preferably has the capability of absorbing liquid which is 20 times or more the weight of the polymer, as well as the property of gelation. Preferable water-absorptive polymer includes starch-acrylic acid (acrylate) graft copolymer, saponificated starch-acrylonitrile copolymer, crosslinked sodium carboxymethyl cellulose, and acrylic acid (acrylate) polymer. Both longitudinal ends of the liquid permeable top sheet 8 are preferably provided with a leakage prevention wall (not shown), wherein the elastic members are provided in a stretched manner along the respective upper side edges of the leakage prevention walls. The leakage prevention wall is formed from a nonwoven fabric cloth, thereby preventing leakage of body fluids absorbed by an absorbent core from both sides of the absorbent core.

The absorbent 5 is placed at the center of the surface of the inner layer sheet 3 facing a wearer and at an intermediate section between the pair of leg opening sections 13 and is bonded to the inner layer sheet 3 such that the longitudinal direction of the absorbent is oriented toward the front and rear abdominal regions, 100, 101.

Second Embodiment

Figure 6A:
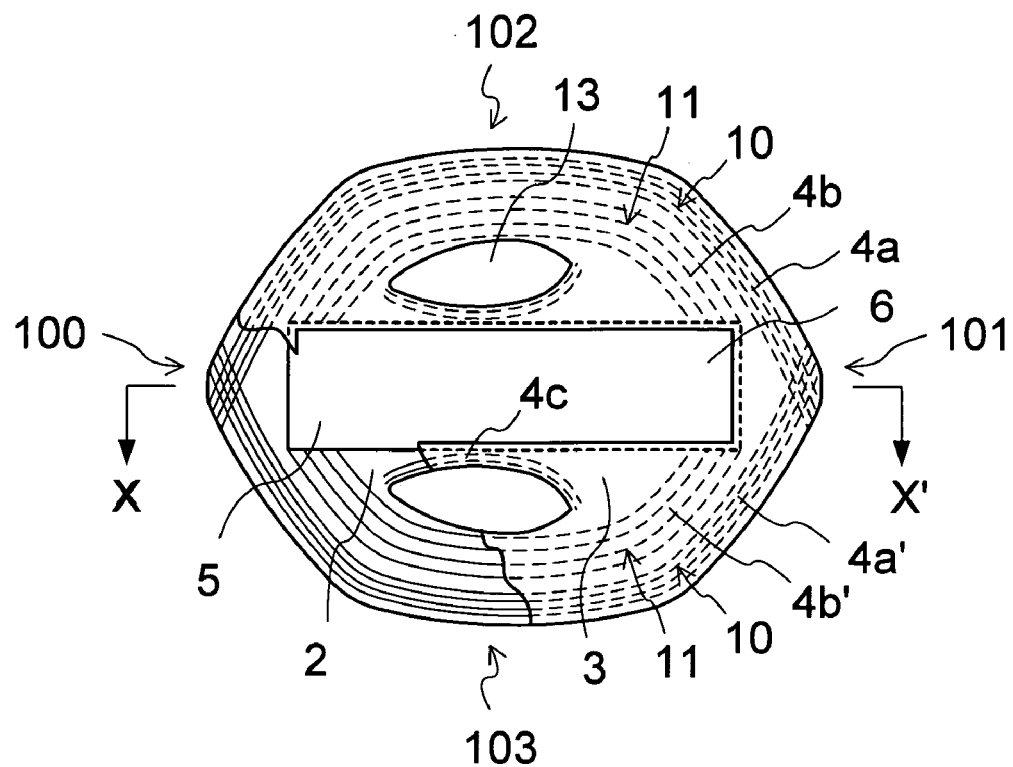
FIG. 6A is a partial fragmentary developed plan view showing second embodiment of the brief-type diaper.
Figure 6B:
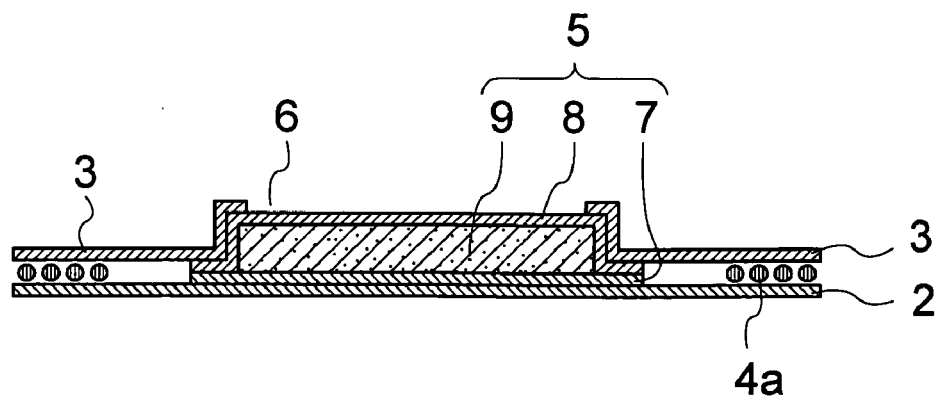
FIG. 6B is a cross-sectional view of the diaper taken along line X–X' shown in FIG. 6A.
Figure 7:
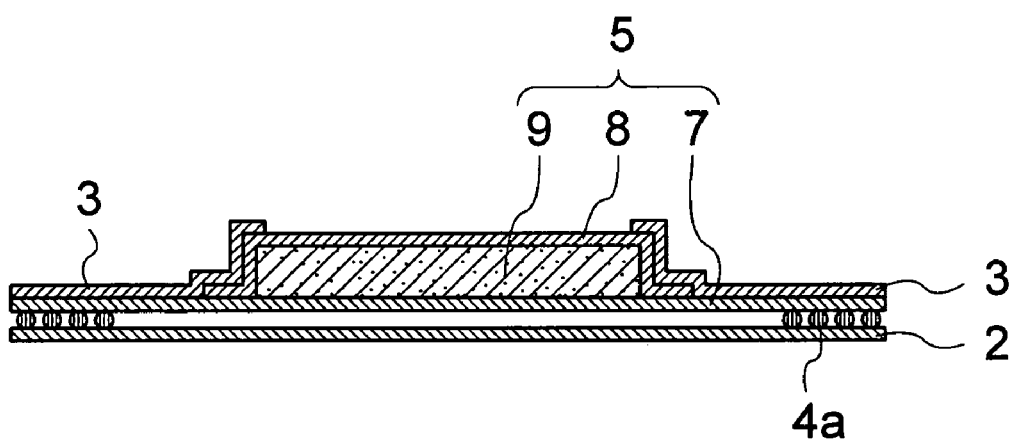
FIG. 7 is a cross-sectional view of a modification of the embodiment shown in FIG. 6 taken along line X–X'.

FIG. 6A is a partial fragmentary developed plan view showing second embodiment of the brief-type diaper, FIG. 6B is a cross-sectional view of the diaper taken along line X–X' shown in FIG. 6A, and FIG. 7 is a cross-sectional view of a modification of the embodiment shown in FIG. 6 taken along line X–X'. In the embodiment, those constituent elements which are the same as those employed in the first embodiment are assigned the same reference numerals, and their repeated explanations are omitted.

As shown in FIGS. 6A and 6B, the brief-type diaper of the second embodiment comprises the outer layer sheet 2 assuming a substantially-circular outer shape; the inner layer sheet 3 which is substantially identical in size and shape with the outer layer sheet 2 and has an opening section 6, the opening section being provided at substantially the center of the inner layer sheet and substantially identical in shape with or slightly smaller size than the absorbent 5; the elastic members 4a, 4a', 4b, 4b' provided between the sheets 2, 3 in a stretched manner; and the absorbent 5 provided at substantially the center of the outer layer sheet 2 in a stacked and cemented manner. More specifically, the absorbent 5 is stacked at substantially the center of the surface of the outer layer sheet 2 facing the wearer and is bonded to the outer layer sheet 2. Further, a plurality of elastic members 4a, 4a' are provided beforehand in a stretched manner so as to follow the outer peripheral edge of the outer layer sheet 2. The outer layer sheet 2 and the inner layer sheet 3 having the opening section 6 formed in the surface of the inner layer sheet 3, which has the elastic members 4a, 4a' and faces the wearer, are formed in an integrated fashion such that the opening section 6 covers the outer peripheral edge of the absorbent 5.

In order to render the waist opening section 10 and girth sections 11 of the diaper elastic, the plurality of elastic members 4a, 4a' are provided between the outer layer sheet 2 and the inner layer sheet 3. Specifically, a plurality of elastic members 4a are provided in a stretched manner across the entire right abdominal region 102 along the waist opening section 10 so as to follow the outer peripheral edge of the outer layer sheet 2. Further, a plurality of elastic members 4a' are provided in a stretched manner in the same manner across the entire left abdominal region 103. Thus, the elastic members 4a, 4a' constitute a waist gather. In addition, a plurality of elastic members 4b are provided in a stretched manner across the entire right abdominal region 102 along the girth, and a plurality of elastic members 4b' are provided in a stretched manner across the entire left abdominal region 103. Thus, the elastic members 4b, 4b' constitute a girth gather.

As shown in FIG. 4A, as in the case of the first embodiment, the plurality of elastic members 4a provided along the waist opening section 10 across the entire right abdominal region 102 and the plurality of elastic members 4a' provided along the waist opening section 10 across the entire left abdominal region 103 are laid in a stretched manner on the continuously-supplied outer layer sheet 2 so as to assume substantial sinusoidal waveforms and such that the elastic members 4a, 4a' cross each other one by one and become tied together. The continuously-supplied inner layer sheet 3 is laid integrally on the surface of the outer layer sheet 2 having the elastic members 4a, 4a' provided in a stretched manner, the surface facing the wearer. The thus-continuously-formed sheet member is finally separated into pieces along areas where the elastic members 4a, 4a' cross each other, thereby forming brief-type diapers. As a result, the elastic members 4a, 4a' cross each other and are connected together at a front abdominal region 100 (abdominal section) and a rear abdominal region 101 (back section), and thus continue along the outer peripheral edges of the outer and inner layer sheets. Further, the elastic members 4a, 4a' are provided beforehand in a stretched manner. Hence, when the elastic members 4a, 4a' provided along the waist opening section 10 in a stretched manner are subjected to contraction, the outer peripheral edges of the outer and inner layer sheets 2, 3 are pulled, thereby constituting a continuous ring-shaped waist opening section 10.

Even in the second embodiment, the outer layer sheet 2 assumes a substantially-circular outer shape, and the curves in which the elastic members 4a, 4a' are laid are set so as to assume a substantial sinusoidal waveform pattern matching the circular shape. However, the shapes of the curves are not limited to such a pattern and may assume any shape, so long as the curves follow curves shown in FIGS. 4A to 4E and the outer shape of the outer layer sheet 2. For instance, if the outer shape of the outer layer sheet 2 assumes a polygonal shape, the curves may assume a kinked line matching the polygonal shape. The elastic members may be connected to each other by an arbitrary method, so long as curves cross each other at respective points or at one point or such that the curves come into contact with each other or come into close proximity to each other.

In the embodiment, the elastic members 4a, 4a' provided along the waist opening section 10 are connected together while crossing each other. As described in detail in connection with the first embodiment, the elastic members may be provided in a stretched manner so as to cross each other at one point, overlap each other in a connected fashion, or come into close proximity to each other. When the elastic members 4a, 4a' are continuously arranged in a stretched manner along the waist opening section 10 and fixedly bonded to the outer layer sheet 2, intersecting portions of the elastic members 4a, 4a' remain non-bonded. When the continuous sheet member is cut along the intersecting portions into brief-type diapers 1, the elastic members 4a, 4a' may be subjected to contraction and be slightly separated from each other become partially discontinuous. In this case, the elastic members 4a, 4a' are partially discontinuous. However, the elastic members 4a, 4a' are laid along the outer peripheral edge of the outer layer sheet 2 in a stretched and substantially continuous fashion. Hence, when the elastic members 4a, 4a' provided along the waist opening section 10 undergo contraction, they constitute a ring-shaped waist opening section 10. In this case, intersections disappear, and hence, the thickness of the elastic members can be reduced as compared with the thickness of the elastic members achieved when intersections are present. Thus, the wearer does not have unusual feeling. The elastic members 4a, 4a' to be laid along the waist opening section 10 in a stretched manner may be provided in a double layer. By means of a double layer structure, fastening the diaper to the waist becomes tight, thereby improving fit. Consequently, even when the diaper has been subjected to vigorous workout, the diaper becomes less likely to slip down.

The elastic members 4b, 4b' provided in the girth 11 are provided at locations outside both side edges of the absorbent 5 in a stretched manner such that elasticity is exhibited. As in the case of the first embodiment, stretching of the elastic members 4b, 4b' is also achieved by laying and fixedly bonding the elastic members 4b, 4b' in the same manner in which the elastic members 4a, 4a' are provided along the waist opening section 10. The elastic members 4b, 4b' are joined together as being provided at areas outside both side edges of the absorbent 5 in a stretched manner. However, the method is not limited to this. The elastic members 4b, 4b' may be joined one by one on the surface of the absorbent 5 facing the wearer. Moreover, the elastic members may be provided in a stretched manner so as to cross or overlap each other at a point. Like the elastic members 4a, 4a' to be provided along the waist opening section 10, intersecting portions of the elastic members 4b, 4b' are not fixedly bonded, whereby the elastic members 4b, 4b' may be made discontinuous. Thus, if the elastic members 4b, 4b' to be provided along the girth 11 in a stretched manner are also provided in a stretched manner at areas where the absorbent is present, both longitudinal ends of the absorbent 5 are pressed by the elastic members 4b, 4b' to the body side. For this reason, adhesion between the diaper and the body is improved, thereby preventing leakage of body fluids such as urine to a much greater extent. Moreover, excessive protrusion of the absorbent is prevented, thereby imparting neat and good appearance to a brief-type diaper.

Up to this point, a description has been given of a case where the elastic members cross each other at the front and rear abdominal regions, 100, 101. The elastic members may cross each other at the right and left abdominal regions 102, 103. Even in this case, the outer layer sheet 2 and the inner layer sheet 3 assume a substantially-circular outer shape. Hence, a brief-type diaper 1 similar to that achieved in the embodiment is formed.

The elastic members 4a, 4a' to be provided along the waist opening section 10 of the outer layer sheet 2 and the elastic members 4b, 4b' to be provided along the girth 11 section of the same may preferably be stretched so as to differ from each other in terms of degree of extension and stress. Specifically, the elastic members 4a, 4a' to be provided along the waist opening section 10 may preferably be stretched with a higher degree of extension and increased stress. Further, the elastic members 4b, 4b' to be provided along the girth 11 section of the outer layer sheet 2 may preferably be stretched with a low degree of extension and small stress.

As mentioned above, the elastic members are extended such that the degree of extension and stress change from the waist opening section 10 to the girth 11, thereby enabling the diaper to conform more closely to the shape of the body. Specifically, the waist opening section 10 of the diaper can be fastened to such an extent that a diaper does not slip down when being worn and conforms to the wearer. Since the girth 11 can gently conform to the wearer, this manner of changing the fit of the diaper; i.e., stretching the elastic members, is preferable. A method for changing the fit of the waist opening section 10 of the diaper and that of the girth 11 may also be achieved by selecting the number of elastic members 4a, 4a', 4b, 4b', intervals at which the elastic members are to be stretched, the thickness of the elastic members, and materials of the elastic members, as required, rather than changing the degree of extension of the elastic members.

In the embodiment, the elastic members to be provided along the waist opening section 10 and those to be provided along the girth 11 are set so as to differ from each other in terms of the degree of extension and stress. However, the same degree of extension or the same stress may also be employed.

A pair of the leg opening sections 13 are formed at positions on the outer and inner layer sheets 2, 3, wherein the positions are symmetrical about the absorbent 5. A plurality of elastic members 4c to be used for forming a leg gather are provided in a stretched manner along the side edge of each leg opening section 13, the side edge facing a crotch region. Adoption of the construction is effective for enhancing adhesion of the leg gather to the neighborhood of the leg 12 and preventing leakage of urine from the space surrounding the legs 12.

Both longitudinal ends of the liquid permeable top sheet 8 of the absorbent 5 are preferably provided with a leakage prevention wall (not shown), wherein the elastic members are provided in a stretched manner along the respective upper side edges of the leakage prevention walls. The leakage prevention wall is formed from a nonwoven fabric cloth, thereby preventing leakage of body fluids absorbed by an absorbent core from both sides of the absorbent core.

As shown in FIG. 7, the liquid-impervious back sheet 7 constituting the absorbent 5 may be made substantially identical in size and shape with the outer layer sheet 2 and interposed between the elastic member 4a, 4a',4b, 4b' and the inner layer sheet 3 in a stretched manner. More specifically, the outer layer sheet 2, the elastic member 4a, 4a',4b, 4b', the liquid-impervious back sheet 7, and the inner layer sheet 3 may be stacked in this order. As a result, the liquid-impervious back sheet 7 is stretched to positions outside both longitudinal sides of the absorbent 5, thereby preventing seepage of the body fluids even if body fluids, such as urine, absorbed by the absorbent core may have leaked.

Third Embodiment

Figure 8A:
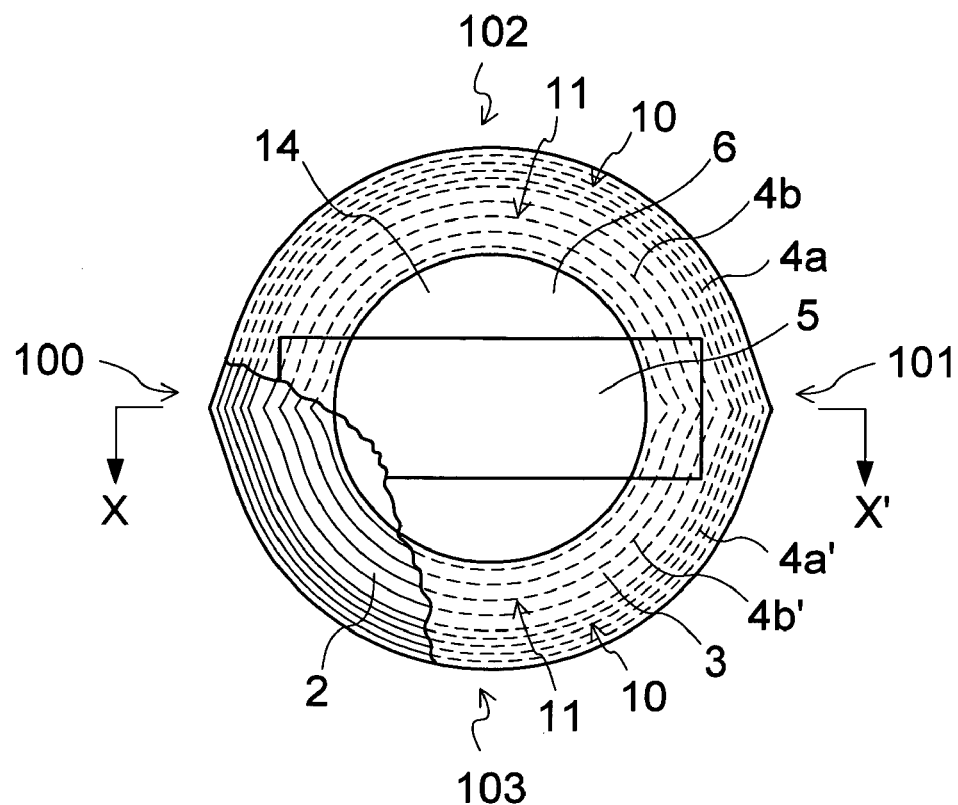
FIG. 8A is a partial fragmentary developed plan view showing a developed sate of third embodiment of the brief-type diaper.
Figure 8B:
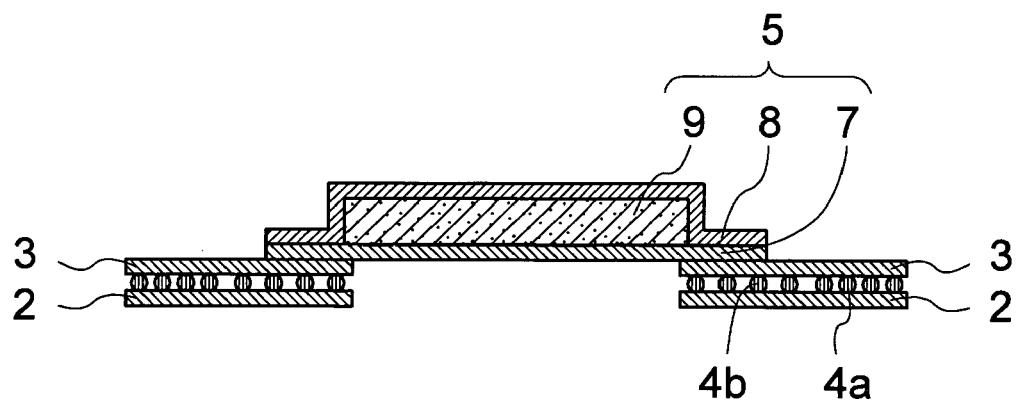
FIG. 8B is a cross-sectional view of the diaper taken along line X–X' shown in FIG. 8A.
Figure 9:
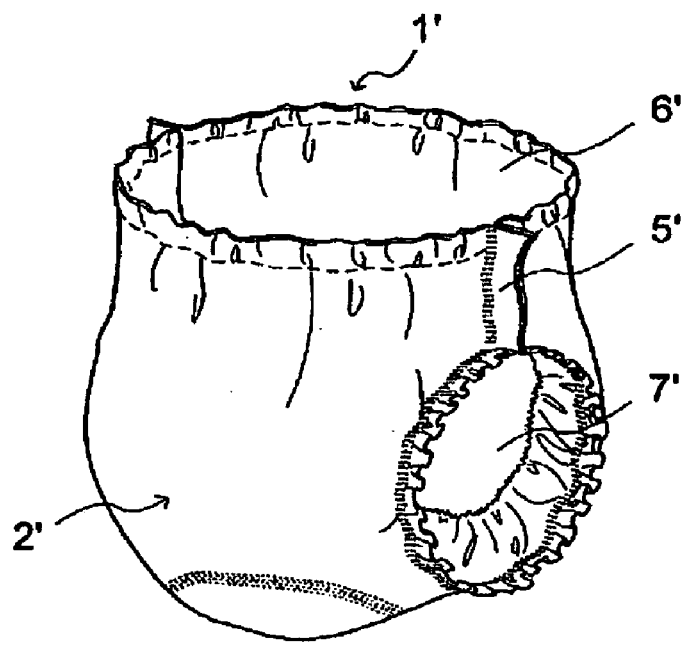
FIG. 9 is a perspective view showing a conventional brief-type diaper.
Figure 10:
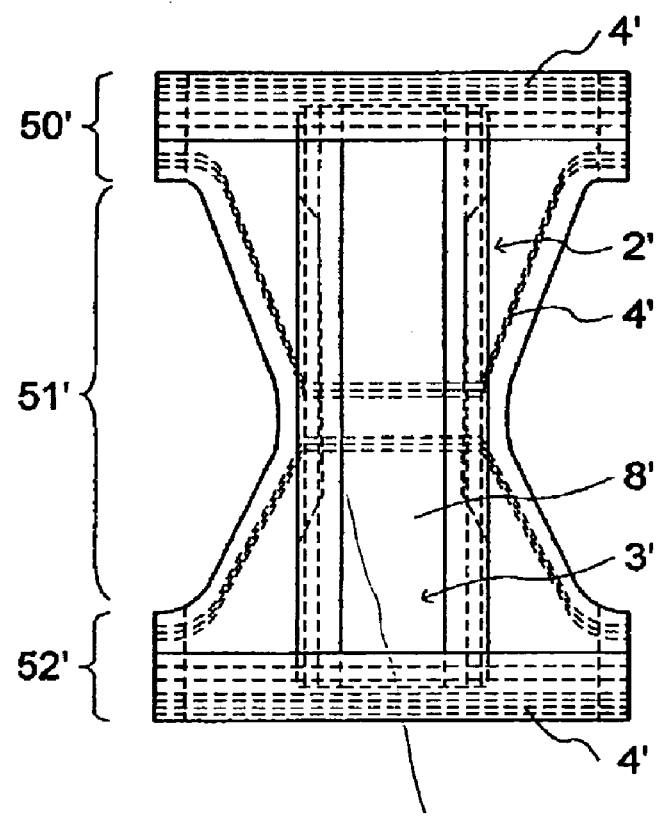
FIG. 10 is a developed plan view showing a developed state of a conventional brief-type diaper.

FIG. 8A is a partial fragmentary developed plan view showing a developed sate of third embodiment of the brief-type diaper and FIG. 8B is a cross-sectional view of the diaper taken along line X–X' shown in FIG. 8A. In the embodiment, those constituent elements which are the same as those employed in the first embodiment are assigned the same reference numerals, and their repeated explanations are omitted.

As shown in FIGS. 8A and 8B, the brief-type diaper of the third embodiment comprises the donut-shaped outer layer sheet 2 assuming a substantially-circular outer shape, the substantially-circular opening section 6 being formed in substantially the center of the outer layer sheet 2; the donut-shaped inner layer sheet 3 which is substantially identical in size and shape with the outer layer sheet 2 and has a substantially-circular opening section 6 provided at substantially the center of the inner layer sheet 3; the elastic members 4a, 4a', 4b, 4b' provided between the sheets 2, 3 in a stretched manner; and the absorbent 5 which is provided at substantially the center of the opening section 6 formed in the surface of the inner layer sheet 3 facing the wearer so as to straddle the opening section 6 and whose longitudinal ends are fixedly cemented to the inner layer sheet 3. More specifically, the inner layer sheet 3 is provided integrally on the surface of the outer layer sheet 2 facing the wearer such that the opening sections 6 coincide with each other. Further, the plurality of elastic members 4a, 4a' 4b, 4b' are provided beforehand between the outer layer sheet 2 and the inner layer sheet 3 in a stretched manner so as to follow the outer peripheral edge of the outer layer sheet 2. The absorbent 5 is provided on the surface of the inner sheet 3 facing the wearer and at substantially the center of the opening section 6 so as to straddle the opening section 6. Both longitudinal ends of the absorbent 5 are fixedly bonded to the inner layer sheet 3. Opening sections 14 are left on both sides of the absorbent 5. Although the absorbent 5 is provided on the surface of the inner layer sheet 3 facing the wearer, the manner of placing the absorbent 5 is not limited to such a manner. The absorbent 5 may be placed such that longitudinal ends of the absorbent are sandwiched between the outer layer sheet 2 and the inner layer sheet 3. When the absorbent 5 is sandwiched between the outer layer sheet 2 and the inner layer sheet 3, the opening section 6 must be formed beforehand in the outer layer sheet 2 and the inner layer sheet 3, respectively, although the opening section are preferably provided from a work surface to the surface of the inner layer sheet 3 facing the wearer so that, the outer layer sheet 2 and the inner layer sheet 3 are formed in an integrated fashion, if the absorbent 5 is placed onto the surface of the inner layer sheet 3 facing the wearer.

In this way, in order to render the waist opening section 10 and girth 11 sections of the diaper elastic, the plurality of elastic members 4a are provided between the outer layer sheet 2 and the inner layer sheet 3. Specifically, a plurality of elastic members 4a are provided in a stretched manner across the entire right abdominal region 102 along the waist opening section 10 so as to follow the outer peripheral edge of the outer layer sheet 2. Further, a plurality of elastic members 4a' are provided in a stretched manner in the same manner across the entire left abdominal region 103. Thus, the elastic members 4a, 4a' constitute a waist gather. In addition, a plurality of elastic members 4b are provided in a stretched manner across the entire right abdominal region 102 along the girth 11, and a plurality of elastic members 4b' are provided in a stretched manner across the entire left abdominal region 103. Thus, the elastic members 4b, 4b' constitute a girth gather.

As shown in FIG. 4A, as in the case of the first embodiment, the plurality of elastic members 4a provided along the waist opening section 10 across the entire right abdominal region 102 and the plurality of elastic members 4a' provided along the waist across the entire left abdominal region 103 are laid in a stretched manner on the continuously-supplied outer layer sheet 2 so as to assume substantial sinusoidal waveforms and such that the elastic members 4a,4a' cross each other one by one and become tied together. The continuously-supplied inner layer sheet 3 is laid integrally on the surface of the outer layer sheet 2 having the elastic members 4a, 4a' provided in a stretched manner, the surface facing the wearer. The thus-continuously-formed sheet member is finally separated into pieces along areas where the elastic members 4a, 4a' cross each other, thereby forming brief-type diapers 1. As a result, the elastic members 4a, 4a' cross each other and are connected together at a front abdominal region 100 (i.e., an abdominal section) and a rear abdominal region 101 (i.e., a back section), and thus continue along the outer peripheral edges of the outer and inner layer sheets. Further, the elastic members 4a, 4a' are provided beforehand in a stretched manner. Hence, when the elastic members 4a, 4a' provided along the waist opening section 10 in a stretched manner are subjected to contraction, the outer peripheral edges of the outer and inner layer sheets 2, 3 are pulled, thereby constituting a continuous ring-shaped waist opening section 10.

Even in the third embodiment, the outer layer sheet 2 assumes a substantially-circular outer shape, and the curves in which the elastic members 4a, 4a' are laid are set so as to assume a substantial sinusoidal waveform pattern matching the circular shape. However, the shapes of the curves are not limited to such a pattern but may assume any shape, so long as the curves follow curves shown in FIGS. 4A to 4E and the outer shape of the outer layer sheet 2. For instance, if the outer shape of outer layer sheet 2 assumes a polygonal shape, the curves may assume a kinked line matching the polygonal shape. Any manner of connecting the elastic members together may be employed, so long as curves cross each other at respective points or at one point or such that the curves come into contact with each other or come into close proximity to each other.

In the embodiment, the elastic members 4a, 4a' provided along the waist opening section 10 are connected together while crossing each other. As described in detail in connection with the first embodiment, the elastic members may be provided in a stretched manner so as to cross each other at one point, overlap each other in a connected fashion, or come into close proximity to each other. When the elastic members 4a, 4a' are continuously arranged in a stretched manner along the waist opening section 10 and fixedly bonded to the outer layer sheet 2, intersecting portions of the elastic members 4a, 4a' remain non-bonded. When the continuous sheet member is cut along the intersecting portions into brief-type diapers, the elastic members 4a, 4a' may be subjected to contraction and be slightly separated from each other (become partially discontinuous). In this case, the elastic members 4a, 4a' are partially discontinuous. However, the elastic members 4a, 4a' are laid along the outer peripheral edge of the outer layer sheet 2 in a stretched and substantially continuous fashion. Hence, when the elastic members 4a, 4a' provided along the waist opening section 10 undergo contraction, they constitute a ring-shaped waist opening section 10. In this case, intersections disappear, and hence, the thickness of the elastic members 4a, 4a' can be reduced as compared with the thickness of the elastic members achieved when intersections are present. Thus, the wearer does not have unusual feeling. The elastic members 4a, 4a' to be laid along the waist opening section 10 in a stretched manner may be provided in a double layer. By means of a double layer structure, fastening the diaper to the waist opening section 10 becomes tight, thereby improving fit. Consequently, even when the diaper has been subjected to vigorous workout, the diaper becomes less likely to slip down.

As in the case of the elastic member 4a, 4a' of waist opening section 10, the elastic members 4b, 4b' provided in the girth 11 are provided along peripheral edge of outer layer sheet 2 in a stretched manner such that elasticity is exhibited. As in the case of the first embodiment, stretching of the elastic members 4b, 4b' is also achieved by laying and fixedly bonding the elastic members 4b, 4b' in the same manner in which the elastic members 4a, 4a' are provided along the waist opening section 10. The elastic members 4b, 4b' are joined together as being provided at areas outside of both side edges of the absorbent 5 in a stretched manner. However, the method is not limited to this. The elastic members 4b, 4b' may be joined one by one on the surface of the absorbent 5 facing the wearer. Moreover, the elastic members may be provided in a stretched manner so as to cross or overlap each other at a point. Like the elastic members 4a, 4a' to be provided along the waist opening section 10, intersecting portions of the elastic members 4b, 4b' are not fixedly bonded, whereby the elastic members 4b, 4b' may be made discontinuous. Thus, if the elastic members 4b, 4b' to be provided along the girth 11 in a stretched manner are also provided in a stretched manner at areas where the absorbent 5 is present, both longitudinal ends of the absorbent 5 are pressed by the elastic members 4b, 4b'. For this reason, adhesion between the diaper and the body is improved, thereby preventing leakage of body fluids such as urine to a much greater extent. Moreover, excessive protrusion of the absorbent 5 is prevented, thereby imparting neat and good appearance to a brief-type diaper.

As in the case of the first embodiment, the elastic members 4b, 4b' may be provided at locations outside both side edges of the absorbent 5 in a stretched manner such that elasticity is exhibited.

Up to this point, a description has been given of a case where the elastic members 4a, 4a', 4b, 4b' cross each other at the front and rear abdominal regions, 100 101. The elastic members may cross each other at the right and left abdominal regions 102, 103. Even in this case, the outer layer sheet 2 and the inner layer sheet 3 assume a substantially-circular outer shape. Hence, a brief-type diaper 1 similar to that achieved in the embodiment is formed.

The elastic members 4a, 4a' to be provided along the waist opening section 10 of the outer layer sheet 2 and the elastic members 4b, 4b' to be provided along the girth 11 section of the same may preferably be stretched so as to differ from each other in terms of degree of extension and stress. Specifically, the elastic members 4a, 4a' to be provided along the waist opening section 10 may preferably be stretched with a higher degree of extension and increased stress. Further, the elastic members 4b, 4b' to be provided along the girth 11 section of the outer layer sheet 2 may preferably be stretched with a low degree of extension and small stress.

As mentioned above, the elastic members 4a, 4a', 4b, 4b' are extended such that the degree of extension and stress changes from the waist opening section 10 to the girth 11, thereby enabling the diaper to conform more closely to the shape of the body. Specifically, the waist opening section 10 of the diaper can be fastened to such an extent that a diaper does not slip down when being worn and conforms to the wearer. Since the girth 11 can gently conform to the wearer, this manner of changing the fit of the diaper; stretching the elastic members, is preferable. The effect can also be achieved by selecting the number of elastic members 4a, 4a',4b, 4b', intervals at which the elastic members are to be stretched, the thickness of the elastic members, and materials of the elastic members, as required, rather than changing the degree of extension and stress of the elastic members.

In the embodiment, the elastic members 4a, 4a',4b, 4b' to be provided along the waist opening section 10 and those to be provided along the girth 11 are set so as to differ from each other in terms of the degree of extension and stress. However, the same degree of extension or the same stress may also be employed.

Both longitudinal ends of the liquid permeable top sheet 8 of the absorbent 5 are preferably provided with a leakage prevention wall (not shown), wherein the elastic members are provided in a stretched manner along the respective upper side edges of the leakage prevention walls. The leakage prevention wall is formed from a nonwoven fabric cloth, thereby preventing leakage of body fluids absorbed by an absorbent core from both sides of the absorbent core.

As described above so far in the embodiments, the shape of the outer layer sheet 2 and that of the inner layer sheet 3 assume a substantially circular shape. However, the shape of these sheets is not limited to substantially circular. The sheets may assume a substantially polygonal shape of three sides (triangular) or more; for example, a substantially square shape, a substantially hexagonal shape, or a substantially octagonal shape. Moreover, the sheets may assume an oval shape. The shapes may be selected according to a wearer or an application, as required.

The brief-type diaper of the invention described in any of the embodiments does not have any cemented section. In contrast to the conventional brief-type diaper, the diaper cannot be torn along the cemented section after having been used. For this reason, means which enable occurrence of a rip is preferably provided in at least a part of the girth 11 although it is not shown in the figure. For example, the means which enables occurrence of a rip may be implemented by perforating the outer layer sheet or inflicting onto the outer layer sheet damage which enables occurrence of a rip, by means of heat fusing using ultrasonic waves.

As mentioned above, in the embodiments the brief-type diaper 1 is formed in the previously-described manner. Hence, the diaper has the following superior productivity. First, either the outer sheet 2 or the inner layer sheet 3, or both of them are seamless and not cemented along an abdominal side section or a rear side section. Hence, the diaper does not have a cemented section which extends from both leg opening sections 13 provided in the girth 11 section to the waist section opening 10. For this reason, even when having worn the diaper 1, the user does not feel any unusual feeling. Further, when the wearer breaks the brief-type diaper while pinching a portion located between the leg opening section 13 and the waist opening section 10, the wearer can easily broaden the diaper and smoothly break the same, because no cemented section exists in the diaper. Further, the diaper does not have any cemented section, and hence the diaper has good, superior appearance.

The brief-type diaper of the invention is not limited to those described in connection with the embodiments. The diaper is susceptible to modifications within the range of the invention. Further, the shape and material of the brief-type diaper are not limited to those described in the connection with the embodiments.

As has been described, a brief-type diaper of the invention comprises stretched elastic members which are provided continuously along an outer peripheral edge of the outer layer sheet in the waist opening section. When the elastic members are subjected to contraction, the outer peripheral edge of outer layer sheet/inner layer sheet is pulled, thereby constituting a continuous ring-shaped waist opening section. Accordingly, the front and rear abdominal regions and the right and left abdominal regions are continuous. In contrast with a conventional brief-type diaper having cemented sections formed by fixedly cementing together an abdominal section and a back section, the brief-type diaper has good appearance and does not cause a wearer to have unusual feeling, which would otherwise be caused when the wearer wears the diaper. Moreover, the diaper has a product characteristic of easily allowing an infant or the like to wear the diaper of the invention, because no cemented section is provided on the diaper.

Further, the elastic members are provided beforehand in a stretched manner such that the front and rear abdominal regions and the right and left abdominal regions are continuous. The elastic members undergo contraction, thereby forming a waist opening section and a girth section. Thus, the diaper conforms to the shape of the wearer's body. In contrast, the outer layer sheet not having elastic members provided therein does not undergo contraction and hence attempts to draw an arc. In this case, the sheet and absorbent of the outer layer sheet possess rigidity, and the sheet and absorbent become three-dimensionally curved, thus assuming the shape of a dome. Consequently, a space is defined in a crotch section. The space enables accumulation of excretions, thereby yielding the effect of preventing leakage and keeping excretions apart from the wearer's skin.

What is claimed is:

1. A brief-type diaper, comprising:
an outer sheet defining an exterior of the diaper;
an inner sheet adapted to come into contact with a wearer;
an absorbent for absorbing body fluids;
an elastic member for causing portions of the outer and inner sheets to form a waist opening when said elastic member contracts; and
a pair of leg openings;
wherein
at least a portion of the absorbent is located between the leg openings;
at least one of the outer and inner sheets has a seamless curved peripheral edge which defines a seamless circumferential edge of the waist opening;
the elastic member extends along substantially an entirety of said peripheral edge;
the inner sheet has an opening in a central region thereof, said absorbent being exposed through said opening; and
said absorbent comprises a back sheet substantially identical in size and shape to the outer sheet and placed between the elastic member and the inner sheet.

2. A brief-type diaper, comprising:
an outer sheet defining an exterior of the diaper;
an inner sheet adapted to come into contact with a wearer;
an absorbent for absorbing body fluids;
elastic members for causing portions of the outer and inner sheets to form a waist opening when said elastic members contract; and
a pair of leg openings;
wherein
at least a portion of the absorbent is located between the leg openings;
at least one of the outer and inner sheets has a seamless peripheral edge which defines a seamless circumferential edge of the waist opening; and
the elastic members cross each other either in front and rear abdominal regions of said diaper along the circumferential edge of the waist opening, or in right and left abdominal regions of said diaper along the circumferential edge of the waist opening.

3. The brief-type diaper according to claim 2, wherein the elastic member is sandwiched between the inner sheet and the outer sheet.

4. The brief-type diaper according to claim 3, further comprising a liquid-impervious sheet provided between the outer sheet and the inner sheet in a central region of said inner and outer sheets.

5. The brief-type diaper according to claim 2, wherein the elastic members comprise at least one selected from the group consisting of rubber yarn, flat rubber, and a ribbon-shaped elastic body.

6. The brief-type diaper according to claim 2 wherein the absorbent is bonded to a wearer facing surface of either the outer sheet or the inner sheet.

7. The brief-type diaper according to claim 2 wherein the absorbent comprises a liquid-pervious top sheet, and an absorbent core placed adjacent to the top sheet for absorbing the body fluids having passed through the top sheet; and
leakage prevention walls are provided along longitudinal side edges of the top sheet.

* * * * *